United States Patent
Liu

(10) Patent No.: US 9,990,717 B2
(45) Date of Patent: Jun. 5, 2018

(54) HEMOGLOBIN AND HEMATOCRIT ANALYZER AND ANALYZING METHOD THEREOF

(71) Applicant: PINGTUNG CHRISTIAN HOSPITAL, Pingtung (TW)

(72) Inventor: Po-Ping Liu, Pingtung (TW)

(73) Assignee: Pingtung Christian Hospital, Pingtung (TW)

(*) Notice: Subject to any disclaimer, the term of this patent is extended or adjusted under 35 U.S.C. 154(b) by 0 days. days.

(21) Appl. No.: 15/446,719

(22) Filed: Mar. 1, 2017

(65) Prior Publication Data

US 2017/0256053 A1    Sep. 7, 2017

(30) Foreign Application Priority Data

Mar. 3, 2016    (TW) .............................. 105106477 A

(51) Int. Cl.
| | | |
|---|---|---|
| G06K 9/00 | (2006.01) |
| G06T 7/00 | (2017.01) |
| G06T 7/90 | (2017.01) |
| A61B 5/145 | (2006.01) |
| A61B 5/00 | (2006.01) |

(52) U.S. Cl.
CPC ............ *G06T 7/0012* (2013.01); *A61B 5/002* (2013.01); *A61B 5/0022* (2013.01); *A61B 5/14535* (2013.01); *A61B 5/14546* (2013.01); *G06T 7/90* (2017.01); *G06T 2207/10024* (2013.01)

(58) Field of Classification Search
CPC ... A61B 5/002; A61B 5/0022; A61B 5/14535; A61B 5/14546; G06T 2207/10024; G06T 7/0012; G06T 7/90
USPC .......................................................... 382/134
See application file for complete search history.

(56) References Cited

U.S. PATENT DOCUMENTS

2013/0293842 A1* 11/2013 Grenon .................. A61B 3/101
    351/206

* cited by examiner

*Primary Examiner* — Manuchehr Rahmjoo
(74) *Attorney, Agent, or Firm* — Wang Law Firm, Inc.

(57) ABSTRACT

Described is a hemoglobin and hematocrit analyzer, and an analyzing method thereof. The method includes: scanning and taking an image signal of the palpebral conjunctiva of a subject by a scanning unit; receiving the image signal by an analyzing unit connected to the scanning unit; providing a default colorimetric scale by a database connected to the analyzing unit; inputting a clinical test result into the analyzing unit through an input unit connected to the analyzing unit. The image signal is transformed by the analyzing unit to a measured color value. The measured color value is compared with the default colorimetric scale to obtain a test result. The measured color value and the clinical test result are provided as feedback to the database.

11 Claims, 3 Drawing Sheets

HEMOGLOBIN AND HEMATOCRIT ANALYZER AND ANALYZING METHOD THEREOF

CROSS-REFERENCE TO RELATED APPLICATION

This application claims priority to and the benefit of Taiwan Patent Application No. 105106477, filed on Mar. 3, 2016, in the Taiwan Intellectual Property Office, the entire content of which is incorporated herein by reference.

BACKGROUND OF THE INVENTION

1. Field of the Invention

The present invention relates to a hemoglobin and hematocrit analyzer, and an analyzing method thereof. Particularly, the present invention relates to an analyzer which is able to analyze the hemoglobin and hematocrit of a patient accurately and give feedback of the test result to the database of the analyzer in order to improve the accuracy of the test.

2. Description of the Related Art

Hemoglobin is a protein present in blood, and the hematocrit is the proportion of erythrocytes contained in a unit volume of blood. Since hemoglobin is a component of erythrocytes, which are also called red blood cells, there is a specific ratio between the amount of hemoglobin and the hematocrit. Hemoglobin concentration and the hematocrit are necessary blood tests in a general blood test panel, as they may be helpful for medical personnel to know the composition of the blood of a patient in order to determine the physiological and biochemical state of the patient. For a patient suffering from severe bleeding, the hemoglobin concentration and the hematocrit may drop rapidly. Hence, the hemoglobin concentration and the hematocrit are important indexes to determine whether a patient needs a blood transfusion or not.

In general clinical medical practice, blood tests for hemoglobin and hematocrit take at least 30 minutes to 1 hour to carry out, not to mention any additional waiting times, such as patient waiting times outside the consulting room prior to blood extraction. However, if the trauma of a patient that has suffered an accident is not obvious then this makes it hard to determine if the patient has suffered from excessive blood loss without a blood test and so it is unknown how long it is safe for the patient to wait for the blood test results. Hence, in an emergency, clinical doctors are only able to determine the patient's blood loss, and therefore need for a blood transfusion, based on their clinical experience and this assessment is generally carried out in urgent emergency situations. Given that the occurrence of human error in this assessment is unavoidable, there is a need to develop a method that takes less time than the conventional blood tests, and which is able to accurately determine the patient's blood loss.

In recent years, point of care testing or bedside testing has become a novel trend in the development of medical diagnostic testing, where the general concept is of a medical diagnostic technology that is able to perform a rapid and efficient analysis at the patient's bedside. Such medical diagnosis technology may be employed at a patient's bedside in a ward or at the point where first aid is being administered, rather than the more traditional method of analyzing samples or specimens in a medical laboratory requiring a wait of hours or days. Point of care medical diagnostic technology has great potential, as it is rapid and efficient with a short test time period for obtaining results or feedback, and, furthermore, is generally simple, low cost, does not require a large amount of sample, and is able to give feedback on the condition of a patient in real-time. Given the advantages in point of care medical diagnosis, it is advantageous to develop and provide a technology for point of care blood testing.

SUMMARY OF THE INVENTION

Following the trend in developing new technologies in point of care medical diagnosis, the purpose of the present invention is to provide an analyzer and an analyzing method thereof for a rapid test of hemoglobin and hematocrit. The analyzer and analyzing method thereof of the present invention is able to rapidly analyze the hemoglobin and hematocrit of the subject, and also give feedback on the test result and the clinical test result. Additionally, the analysis results have drastically increased accuracy and the possibility of installing the analyzer in a mobile device makes it even more practical and convenient to use.

The hemoglobin and hematocrit analyzer and analyzing method thereof of the present invention includes: a scanning unit scanning and taking an image signal of the palpebral conjunctiva of a subject; an analyzing unit connected to the scanning unit and receiving the image signal; a database connected to the analyzing unit; and an input unit connected to the analyzing unit and inputting the clinical test result of the subject. The analyzing unit transforms the image signal to a measured color value, and compares the measured color value with a default colorimetric scale to obtain a test result; and the analyzing unit gives feedback of the measured color value and the clinical test result to the database.

Preferably, the analyzer of the present invention may further include a calibrating unit which may be connected to the analyzing unit and the scanning unit in order to calibrate the chromatic aberration of the image signal.

As mentioned above, the calibrating unit may calibrate the chromatic aberration of the image signal prior to the transformation of the image signal to the measured color value, and obtains a calibrated image signal.

Preferably, the analyzing unit and the database may be disposed in a mobile device, which may receive the image signal and output the test result through a transmission medium.

As mentioned above, the transmission medium may include one or more of, but is not limited to, a mobile network, wireless local area network (WLAN), local area network (LAN) and Bluetooth.

As mentioned above, the mobile device may be selected from the group consisting of: a smartphone, a tablet, a laptop and a smartwatch.

Preferably, the measured color value and the clinical test result of the subject may be given as feedback to the database in order to create another default colorimetric scale.

According to the said purpose, an analyzing method of hemoglobin and hematocrit is also provided, including: taking an image signal of the palpebral conjunctiva of a subject to obtain an image signal; transforming the image signal to a measured color value; comparing the measured color value with a default colorimetric scale to obtain a test result; inputting the clinical test result of the subject; and giving the measured color value and the clinical test result as feedback to the database.

Preferably, the analyzing method of the present invention may further include calibrating the chromatic aberration of the image signal prior to the transformation of the image signal to the measured color value.

Preferably, the analyzing method of the present invention may further include transmitting the image signal and the test result through the transmission medium.

Preferably, the analyzing method may further include creating another default colorimetric scale.

As mentioned above, the hemoglobin and hematocrit analyzer and analyzing method thereof of the present invention may have one or more of the following advantages:

(1) The hemoglobin and hematocrit analyzer and analyzing method thereof provided in the present invention combines an imaging unit and an analyzing unit, which may output the test result in a short time and improve the speed of analysis.

(2) The hemoglobin and hematocrit analyzer and analyzing method thereof provided in the present invention gives a the test result as feedback to the database to increase the sample size, update and create a default colorimetric scale at any time in order to improve the accuracy of the test.

(3) The hemoglobin and hematocrit analyzer and analyzing method thereof provided in the present invention may be installed in a mobile device and operated therefrom, and thereby is easy to use and carry, and advantageous for clinical medical personnel in their health care work.

DETAILED DESCRIPTION OF THE PREFERRED EMBODIMENTS

Hereinafter, the embodiments of the present invention are provided and described in detail with reference to the appended drawings.

A hemoglobin and hematocrit analyzer is provided in the present invention, and includes: a scanning unit scanning a palpebral conjunctiva of a subject and including an imaging unit which is used to take an image signal of the palpebral conjunctiva of a subject; an analyzing unit connected to the scanning unit to receive the image signal; and a database connected to the analyzing unit to provide a default colorimetric scale. The analyzing unit transforms the image signal to a measured color value and compares the measured color value with the default colorimetric scale to obtain a test result; then the analyzing unit outputs the test result; and the analyzing unit gives the measured color value and the test result as feedback to the database.

Figure 1:
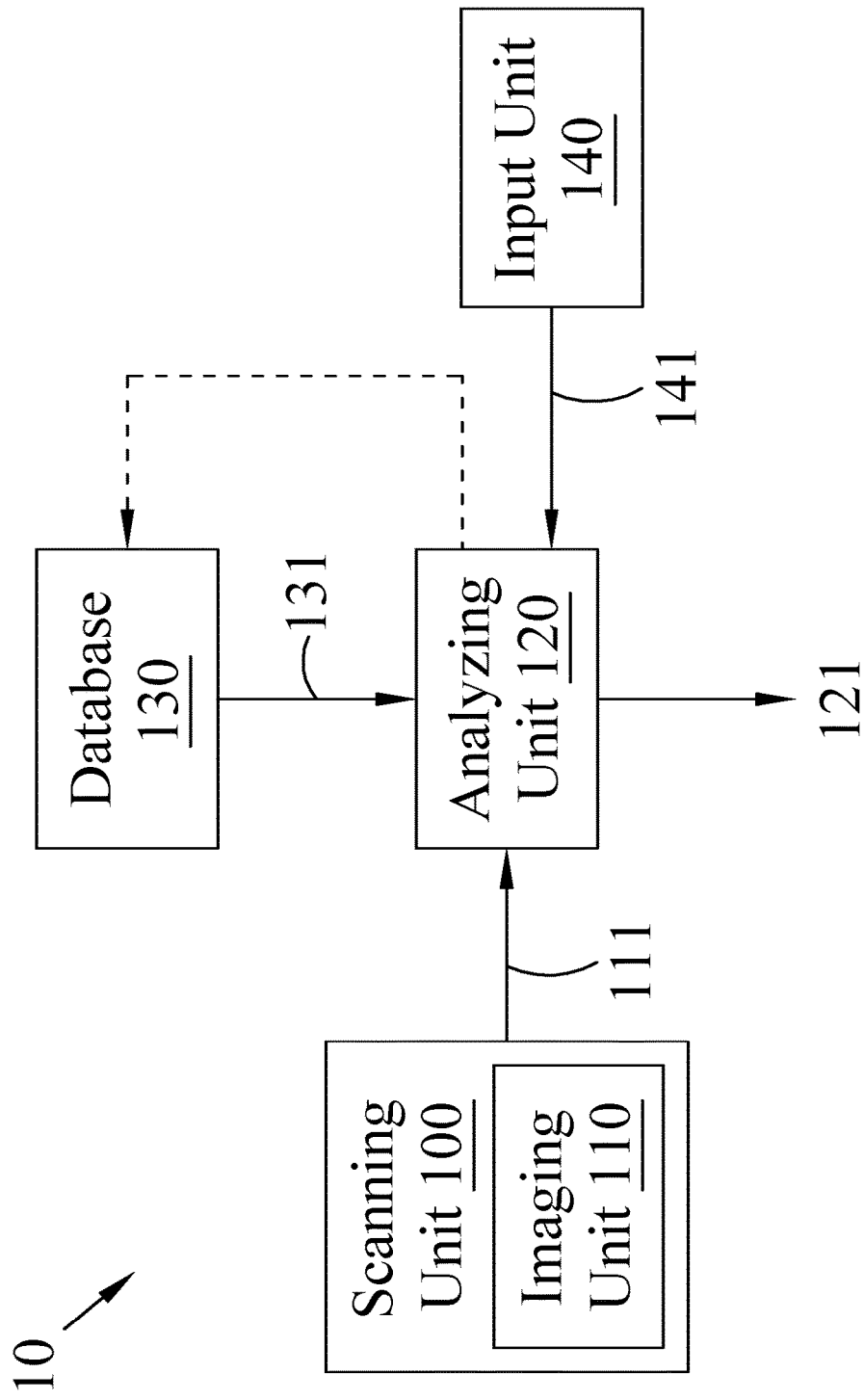
FIG. 1 is a schematic block diagram of the hemoglobin and hematocrit analyzer of the first embodiment of the present invention.

For a detail description, an embodiment of the hemoglobin and hematocrit analyzer of the present invention is here provided, which refers to FIG. 1, a schematic block diagram of the first embodiment of the hemoglobin and hematocrit analyzer of the present invention. The hemoglobin and hematocrit analyzer 10 of the present invention includes a scanning unit 100, an analyzing unit 120, a database 130 and an input unit 140. An imaging unit 110 is included inside the scanning unit 100; the scanning unit 100 is connected to the analyzing unit 120; the database 130 is connected to the analyzing unit 120; and the input unit 140 is connected to the analyzing unit 120.

In particular, the main function of the scanning unit 100 is scanning the palpebral conjunctiva of a subject and taking an image of the palpebral conjunctiva of the subject by the imaging unit 110 to obtain an image signal 111. The image signal 111 is then transmitted to the analyzing unit 120. The analyzing unit 120 receives the image signal 111, which is then transformed to a measured color value. For example, the analyzing unit 120 may transform the digital pattern obtained by the imaging unit 110 to a color value defined by the RGB color model, i.e. the measured color value. However, the analyzing unit in the hemoglobin and hematocrit analyzer of the present invention is not limited to using a color value defined by the RGB color model but may alternatively use other color models such as: the CMYK color model, RYB color model, HSV and HSL model or others.

The database 130 is connected to the analyzing unit 120 and provided with a default colorimetric scale 131. The principle of creating the default colorimetric scale is described hereinafter. First, images of the palpebral conjunctiva from a number of clinical subjects are collected (the sample size should be large enough for statistical significance, e.g. >100 subjects), then each image of the palpebral conjunctiva is defined using the RGB model with a color value. Concurrently, the clinical hemoglobin and hematocrit data of every subject is obtained. Data from all of the subjects are combined and analyzed to yield values of hemoglobin concentration in the range of 5 to 15 g/dL, and a hematocrit range of 15 to 45% (the value of the hematocrit is about 3 times of the value of the hemoglobin concentration, the value of the hematocrit being converted from the value of the hemoglobin concentration). Then, the color value of the image of the palpebral conjunctiva and the directly measured value of hemoglobin concentration and hematocrit are combined, thereby creating a range of colorimetric chromaticities matched with corresponding estimated values of hemoglobin concentrations and hematocrit, i.e. the default colorimetric scale 131. In short, the database 130 has a built-in default colorimetric scale 131 based on data from a large number of clinical subjects. This allows for the aforementioned measured color value, transformed by the analyzing unit 120 from the image signal 111 taken by the imaging unit 110, to be compared with the default colorimetric scale 131, thereby producing a test result 121 of the estimated values of hemoglobin concentration and hematocrit corresponding to the measured color value of the subjects as found in the default colorimetric scale 131.

Table 1 shows an example of a default colorimetric scale, with color values created by the RGB color model and corresponding values of hemoglobin and hematocrit. Since the color value of the image of the palpebral conjunctiva following transformation does not necessarily match the exact values of R, G and B in the table, an interval of ±3 around each value of R, G and B is used to correspond to a pair of values of the estimated hemoglobin concentration and hematocrit found in the table. So by using the default colorimetric scale, the test result may be obtained by simply measuring the color value. For example, if the measured color value of the palpebral conjunctiva of a patient is R167G117B128, the default colorimetric scale is consulted to obtain an estimated hemoglobin concentration of 5 g/dL, and a hematocrit of 15% for the patient. Generally, the hemoglobin concentration of a normal male is 13.0 to 18.0 g/dL; and that of a female is 11.0 to 16.0 g/dL; with hematocrits of 38 to 47%. Hence, the assessment is that the patient requires a blood transfusion.

TABLE 1

| Default colorimetric scale | | | | |
|---|---|---|---|---|
| RGB color model | | | Hemoglobin | Hematocrit |
| R | G | B | (g/dL) | (%) |
| 167 | 117 | 128 | 5 | 15 |
| 164 | 109 | 119 | 6 | 18 |
| 161 | 100 | 107 | 7 | 21 |
| 158 | 92 | 100 | 8 | 24 |
| 156 | 83 | 90 | 9 | 27 |
| 154 | 75 | 81 | 10 | 30 |
| 153 | 67 | 70 | 11 | 33 |
| 151 | 59 | 62 | 12 | 36 |
| 149 | 51 | 52 | 13 | 39 |
| 146 | 42 | 41 | 14 | 42 |
| 142 | 24 | 22 | 15 | 45 |

As well as outputting the test result 121, the analyzing unit 120 also receives the outer signal from the input unit 140. In the first embodiment provided in the present invention, the analyzing unit 120 receives medical information of a subject from the input unit 140; that is, medical personnel manually input clinical test result 141 of the subject examined into the input unit 140, and then the input unit 140 then feeds the clinical test result 141 to the analyzing unit 120. This enables the analyzing unit 120 to provide the clinical test result 141 and the measured color value of the subject examined together as feedback to the database 130. The purpose is to increase the sample number of original subjects in the database 130, and to reduce the error level of the test result 121 produced by the analyzer of the present invention by incorporating the clinical test result 141. After testing each subject, the clinical test result may be combined together with the measured color value in order to increase the sample number of the database 130, and to recalibrate the default colorimetric scale by adjusting the measured color values and produce an new default colorimetric scale, which further improves the accuracy of the default colorimetric scale provided in the present invention.

Figure 2:
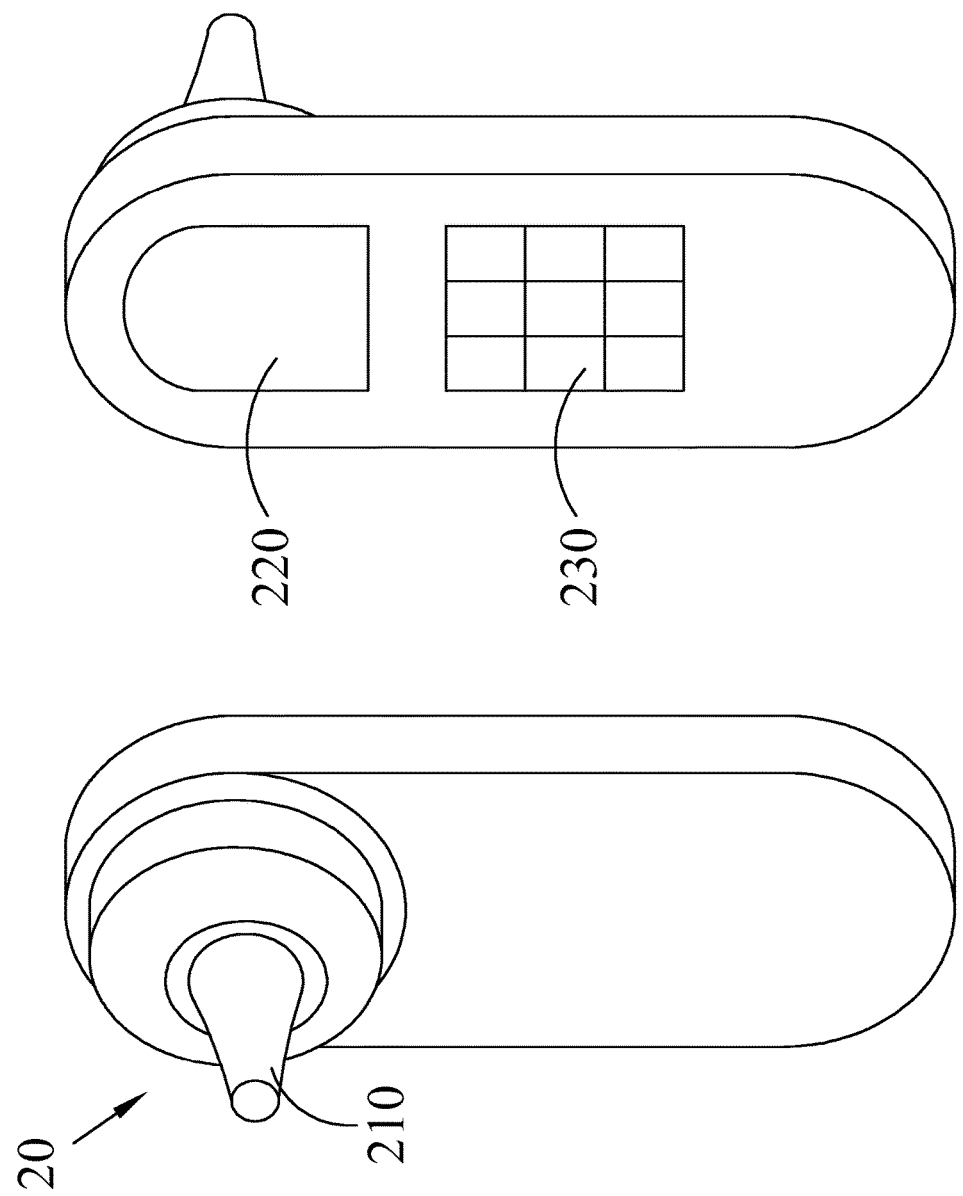
FIG. 2 is a schematic three-dimensional view of an implementation of the hemoglobin and hematocrit analyzer of the first embodiment of the present invention.

The embodiments of the hemoglobin and hematocrit analyzer of the present invention may be installed in a mobile device. FIG. 2 is a schematic three-dimensional view of an implementation of testing apparatus of the hemoglobin and hematocrit analyzer of the first embodiment of the present invention. The drawings are merely provided as example depictions for the purpose of further illustration of the technical features of the present invention, and should not be interpreted to limit the scope of the present invention. First, the testing apparatus 20 has an exposed beak portion and a digital camera lens 210 disposed therein, and a grip portion having a screen 220 and keyboard 230 at the backside of the beak portion. The digital camera lens 210 may take an image of the palpebral conjunctiva of a patient, followed by analysis and comparison through the process shown in FIG. 1 of the analyzer, producing a test result, which may be shown on the screen 220. Furthermore, the clinical test result of the patient may be manually entered through the keyboard 230 to be used as feedback for the database of the analyzer (not shown) in order to reduce the error, and produce a new default colorimetric scale or update the original default colorimetric scale with improved accuracy. The structure of the testing apparatus 20 of the present invention depicted in the schematic diagram of FIG. 2 is one implementation, and one skilled in the art is able to apply equivalent modifications and improvements to the disposition of the elements of the apparatus. For example, a touch screen may be disposed at the grip portion to simultaneously provide a function of displaying the test result and a function of inputting the test result. However, the present invention is not limited thereby.

The first embodiment of the analyzer of the present invention may be implemented as a standalone testing apparatus, or may be installed in different types of mobile devices, such as, but not limited to: smartphones, tablets, laptops and smartwatches. The smartphone is hereinafter described in detail as an example. The analyzer of the present invention may be provided through specific software such as an application or app for short, and installed onto the smartphone. The images are obtained by the camera lens built into the smartphone and the software analyzes the images by comparing the images with the default colorimetric scale provided by the database to obtain a test result. The clinical test result of the patient may also be inputted or manually entered by using the touch screen of the smartphone. Due to the popularity of smartphones, such an implementation is portable, convenient, simple and easy to use, facilitating its use during an emergency, and furthermore, the software may be easily obtained and installed.

In another implementation, the analyzing unit and database may be installed in a smartwatch as a specific application. The image signal is received and the test result may then be outputted through a transmission medium. For example, if, in an emergency, the patient is too far to reach a medical facility in time for urgent treatment, then first-aid personnel on site have to assess whether the patient has suffered severe blood loss and requires a blood transfusion. In this situation, the first-aid personnel on site may take an image of the palpebral conjunctiva of the patient with an imaging unit, then transmit the signal information to the worn smartwatch through a Bluetooth transmission system, for the smartwatch to compare and to analyze the image using the built-in database and the analyzing unit in order to obtain the test result of the hemoglobin and hematocrit of the patient. In this way, the first-aid personnel are able to determine whether the patient urgently requires a blood transfusion. This implementation of the present invention solves the problem where a patient in a remote area has to wait to reach a medical center before the test result is obtained, and so improving the scope of first-aid provision and reducing loss of life.

Figure 3:
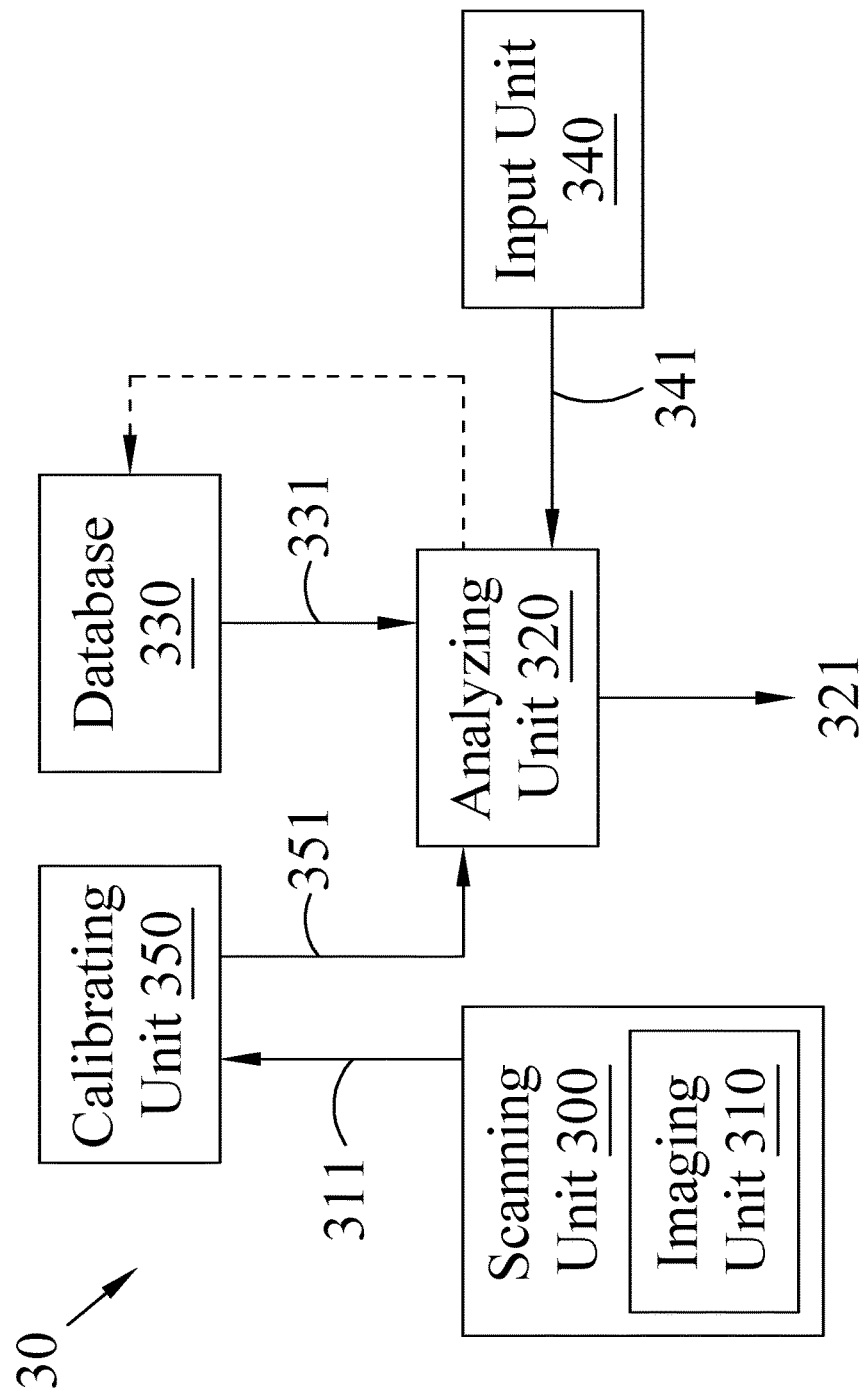
FIG. 3 is a schematic block diagram of the hemoglobin and hematocrit analyzer of the second embodiment of the present invention.

Another embodiment of the hemoglobin and hematocrit analyzer of the present invention is provided, hereafter described in detail, with reference to FIG. 3, which is a schematic block diagram of the hemoglobin and hematocrit analyzer of the second embodiment of the present invention. The analyzer 30 of the second embodiment of the present invention not only includes a scanning unit 300, an imaging unit 310, an analyzing unit 320, a database 330 and an input unit 340 but also includes a calibrating unit 350. The scanning unit 300 includes the imaging unit 310 therein and is connected to the analyzing unit 320; the calibrating unit 350 is connected to the analyzing unit 320 and the scanning unit 300; the database 330 is connected to the analyzing unit 320; and the input unit 340 is connected to the analyzing unit 320.

In particular, the scanning unit 300 (including the imaging unit 310) of the second embodiment of the present invention has a same function as the scanning unit 100 of the first embodiment, where both of them are used to take an image of the palpebral conjunctiva of a patient in order to obtain an image signal 311. Then the image signal 311 is transmitted to the calibrating unit 350. The difference between the first embodiment and the second embodiment of the present invention is that for the second embodiment the chromatic aberration of the image signal 311 is calibrated by the calibrating unit 350 to obtain a calibrated image signal 351 and is then transformed to a measured color value, whereas for the first embodiment the image signal 311 is directly transformed to a measured color value. The calibrated image signal 351 calibrated by the calibrating unit 350 may fix color and brightness deviation of the image caused by man-made error when taking the image. Then, the calibrated image signal 351 is transformed to a color value defined by the RGB color model to produce a measured color value. However, the analyzing unit of the analyzer provided by the present invention may transform the calibrated image signal 315 to a color value defined by color models other than the RGB color model, such as the CMYK color model, RYB color model, HSV, HSL or other color models.

Furthermore, the database 330 is connected to the analyzing unit 320 and provides a default colorimetric scale 331. As with the first embodiment, the images of the palpebral conjunctiva of a number of subjects are taken, where the sample number is statistically significant, and each image is transformed to a color value, which is then included in the database 330. The database 330 further includes the clinical data of the hemoglobin concentration and hematocrit of the subjects. The measured color values and the clinical data of the subjects are combined in the database 330 to produce a default colorimetric scale 331. The default colorimetric scale is produced and used in the same way as in the first embodiment, and details thereof are not repeated here. The test result 321 of the hemoglobin concentration and hematocrit of the subjects may be then obtained by comparing the measured color value, transformed by the analyzing unit 320 from the image taken by the imaging unit 310 and calibrated by the calibrating unit 350, with the default colorimetric scale 331.

Finally, regarding the hemoglobin and hematocrit analyzer provided by the second embodiment of the present invention, wherein the analyzing unit 320 is not only able to compare the information of the measured color value with the default colorimetric scale, but is also able to take manual input of the external signal. More specifically, the analyzer may take an input of the clinical test result 341 of an examined subject and the input unit 340 may feed the clinical test results 341 to the analyzing unit 320. Thus, the clinical test result 341 of the examined subject and the measured color value may be combined and fed as feedback to the database 330. The purpose of this is to increase the sample number of original subjects in the database 330, and to reduce the error level of the test result 321 obtained by the analyzer of the present invention based on the clinical test result 341. Whenever a subject is tested, a clinical test result and a measured color value may be added in order to increase the sample number of the database 330 and also to reduce the error level of the test result 321. Furthermore, the database 330 may, at any time, be calibrated to the default colorimetric scale, or be updated to create a new default colorimetric scale so as to improve the matching accuracy of the default colorimetric scale in the analyzer of the present invention.

The second embodiment of the analyzer provided by the present invention may also be a standalone analyzer, or installed in different types of mobile devices. As mentioned above, for the implementation of the analyzer of the present invention, the mobile device may be a smartphone. The exemplary implementation may be a specific application or app that is installed onto a smartphone. The image may be obtained by a built-in camera lens of the smartphone and the color aberration of the image may be calibrated by a calibrating program, and then the calibrated image is inputted into the application for analysis, which includes comparison with the default colorimetric scale provided by the database, to produce a test result. A clinical test result of the patient may also be inputted through the screen of the smartphone. Due to the popularity of smartphones, this implementation is portable, convenient, simple and easy to use, facilitating its use during an emergency, and furthermore, the software may be easily obtained and installed.

Another implementation involves disposing the analyzing unit and the database at a fixed computer or a computing processing carrier, and receiving the image signal and outputting the test result through a transmission medium. For example, if, in an emergency, the patient is too far to reach a medical facility in time for urgent treatment, then first-aid personnel on site have to assess whether the patient has suffered severe blood loss and requires a blood transfusion. In this situation, the first-aid personnel on site may take an image of the palpebral conjunctiva of the patient with a digital camera, and then transmit the signal information to the database and the analyzing unit in a medical center faraway through a communication network. The test result is then transmitted back to the first-aid personnel so that the first-aid personnel may determine whether the patient urgently needs a blood transfusion. The communication network includes, but is not limited to, a mobile network, WLAN, LAN, WAN or other network technology. The communication unit at the sending and receiving ends may be a landline telephone, a cordless telephone, a satellite telephone or other communication device. This implementation of the present invention also solves the problem where a patient in a remote area has to wait to reach a medical center before the test result is obtained, and so improving the scope of first-aid provision and reducing loss of life.

The invention disclosed herein has been described by means of exemplary embodiments and appended drawings. However, numerous modifications, variations and enhancements can be made thereto by those skilled in the art without changing the essential characteristics or technical spirit of the present invention. Therefore, it is to be understood that the present invention is not limited to the forms described in the exemplary embodiments and appended drawings, rather that the technical and protective scope of the present invention is defined by the following claims.

What is claimed is:

1. A hemoglobin and hematocrit analyzer, comprising:
a scanning unit scanning and taking an image signal of the palpebral conjunctiva of a subject;
an analyzing unit connected to the scanning unit and receiving the image signal;
a database connected to the analyzing unit and providing a default colorimetric scale; and
an input unit connected to the analyzing unit and inputting a clinical test result of the subject,
wherein the analyzing unit transforms the image signal to a measured color value, and the measured color value is compared with the default colorimetric scale to obtain a test result; and
the analyzing unit gives the measured color value as feedback to the database, and the analyzing unit calibrates an error level of the test result according to the clinical test result.

2. The analyzer as in claim 1, further comprising a calibrating unit connected to the analyzing unit and the scanning unit, and calibrating the chromatic aberration of the image signal.

3. The analyzer as in claim 2, wherein the calibrating unit calibrates the chromatic aberration of the image signal and obtains a calibrated image signal prior to the transformation of the image signal to the measured color value.

4. The analyzer as in claim 1, wherein the analyzing unit and the database are disposed in a mobile device, and the device receives the image signal and outputs the test result through a transmission medium.

5. The analyzer as in claim 4, wherein the transmission medium comprises a mobile network, WLAN, LAN and Bluetooth.

6. The analyzer as in claim 4, wherein the mobile device is selected from the group consisting of: a smartphone, a tablet, a laptop and a smartwatch.

7. The analyzer as in claim 1, wherein the measured color value and the clinical test result of the subject are given to the database as feedback, and the measured color value and the clinical test result are used to produce another default colorimetric scale.

8. An analyzing method of hemoglobin and hematocrit, comprising:
    taking an image of the palpebral conjunctiva to obtain an image signal;
    transforming the image signal to a measured color value;
    comparing the measured color value with a default colorimetric scale to obtain a test result;
    inputting a clinical test result of the subject; and
    giving the measured color value and the clinical test result as feedback to a database and calibrating the error level of the test result according to the clinical test result.

9. The method as in claim 8, further comprising calibrating the chromatic aberration of the image signal prior to transforming the image signal to the measured color value.

10. The method as in claim 8, further comprising transmitting the image signal and the test result through a transmission medium.

11. The method as in claim 8, further comprising producing another default colorimetric scale.

\* \* \* \* \*